US008170515B2

(12) United States Patent
Le Reverend et al.

(10) Patent No.: US 8,170,515 B2
(45) Date of Patent: May 1, 2012

(54) METHOD AND APPARATUS FOR THE PHASED DETECTION OF A SIGNAL INCLUDING A FREQUENCY DEVIATION DETECTION PHASE

(75) Inventors: Remi Le Reverend, San Diego, CA (US); Guy A. Delight, Escondido, CA (US); Peter Bradley, San Diego, CA (US)

(73) Assignee: Medtronic, Inc., Minneapolis, MN (US)

( * ) Notice: Subject to any disclaimer, the term of this patent is extended or adjusted under 35 U.S.C. 154(b) by 626 days.

(21) Appl. No.: 12/242,789

(22) Filed: Sep. 30, 2008

(65) Prior Publication Data
US 2009/0291656 A1  Nov. 26, 2009

Related U.S. Application Data

(60) Provisional application No. 61/055,059, filed on May 21, 2008.

(51) Int. Cl.
*H04B 1/16* (2006.01)
(52) U.S. Cl. ............... 455/227; 455/154.1; 455/337
(58) Field of Classification Search ............ 455/150.1, 455/154.1, 161.1, 166.1, 166.2, 205, 214, 455/227, 255, 257, 263, 334, 337
See application file for complete search history.

(56) References Cited

U.S. PATENT DOCUMENTS

| | | |
|---|---|---|
| 4,160,955 A | 7/1979 | Sato |
| 4,194,156 A | 3/1980 | Sakabe |
| 4,562,404 A | 12/1985 | Futakuchi |
| 4,676,248 A | 6/1987 | Berntson |
| 4,777,659 A * | 10/1988 | Lindenmeier et al. ......... 455/296 |
| 4,914,715 A * | 4/1990 | Miyata ........................... 455/212 |
| 5,132,799 A * | 7/1992 | Gakumura ..................... 348/731 |
| 5,350,407 A | 9/1994 | McClure et al. |
| 5,423,085 A * | 6/1995 | Lim ............................ 455/182.2 |
| 6,072,997 A | 6/2000 | Kawai |
| 7,127,218 B2 * | 10/2006 | Lindenmeier ................. 455/101 |
| 2001/0041551 A1 | 11/2001 | Rotzoll |

(Continued)

FOREIGN PATENT DOCUMENTS

EP  0656701  6/1995

(Continued)

OTHER PUBLICATIONS

Zarlink ZL 70100, "Medical Transceiver Data Sheet", May 2005.

(Continued)

*Primary Examiner* — Nhan Le
(74) *Attorney, Agent, or Firm* — Stephen W. Bauer; Michael J. Ostrom (57) ABSTRACT

A plurality of phases of sniff operations are performed for detecting wake-up signals being received by an implantable medical device (IMD), including a phase that performs a staged detection of whether the integrated frequency deviation of a received signal is outside of an expected frequency deviation range, where sniff operations are aborted if the integrated frequency deviation of the received signal falls outside of corresponding high and low thresholds in any stage, wherein the difference between the high and low thresholds tightens with each subsequent stage and an average frequency deviation over all completed stages are used in the calculations. One phase of sniff operations includes a dual frequency modulation (FM) detector including a first FM detector that introduces a small delay in a received signal providing an average frequency estimate and a second FM detector having a larger delay that is adjusted based on the estimated average frequency.

15 Claims, 6 Drawing Sheets

U.S. PATENT DOCUMENTS

| | | |
|---|---|---|
| 2003/0114897 A1 | 6/2003 | Von Arx et al. |
| 2003/0114898 A1 | 6/2003 | Von Arx et al. |
| 2003/0119568 A1 | 6/2003 | Menard |
| 2004/0014480 A1* | 1/2004 | Liu et al. ................ 455/502 |
| 2004/0077383 A1 | 4/2004 | Lappetelainen et al. |
| 2004/0133092 A1 | 7/2004 | Kain |
| 2004/0207464 A1 | 10/2004 | Petrovic et al. |
| 2005/0150949 A1 | 7/2005 | Goel et al. |
| 2006/0229053 A1 | 10/2006 | Sivard |
| 2007/0049991 A1 | 3/2007 | Klostermann et al. |
| 2007/0060053 A1 | 3/2007 | Haubrich et al. |
| 2007/0060976 A1 | 3/2007 | Denzene et al. |
| 2007/0153705 A1 | 7/2007 | Rosar et al. |
| 2008/0046038 A1 | 2/2008 | Hill et al. |
| 2008/0048836 A1 | 2/2008 | Bungartz et al. |
| 2009/0248116 A1 | 10/2009 | Le Reverend et al. |

FOREIGN PATENT DOCUMENTS

| | | |
|---|---|---|
| EP | 1264614 | 12/2002 |

OTHER PUBLICATIONS

International Search Report, PCT/US2009/044445, 4 pages.

* cited by examiner

1) *No wake-up signal present - No false alarm*

2) *Some signal present in channel 4 - Wrong frequency deviation*

3) *Some signal present in channel 4 - Wrong content*

4) *Valid signal present in channel 4*

METHOD AND APPARATUS FOR THE PHASED DETECTION OF A SIGNAL INCLUDING A FREQUENCY DEVIATION DETECTION PHASE

RELATED APPLICATION

This application claims the benefit of and priority to U.S. Provisional Application Ser. No. 61/055,059, filed May 21, 2008, entitled, "Method and Apparatus for the Phased Detection of a Signal Including a Frequency Deviation Detection Phase," the contents of which are incorporated by reference herein in its entirety.

TECHNICAL FIELD

This disclosure relates generally to implantable medical devices (IMDs) and more particularly to IMDs capable of telemetry.

BACKGROUND

A wide variety of IMDs have been developed in order to monitor patient conditions and deliver therapy to the patient. An IMD typically includes a hermetically sealed housing coupled to one or more leads that are surgically implanted inside a patient for sensing conditions or for administering therapy. The IMD may provide therapeutic stimulation to the patient or may deliver drugs or agents to the patient. Alternatively or additionally, the IMD may have sensing or monitoring capabilities. For example, the IMD may sense information within a patient and store the sensed information for subsequent analysis. In some cases, the sensed information may be used directly by the IMD to adjust or control the therapy that is delivered to the patent. Telemetry is used to communicate sensed information from the IMD to an external medical device so that analysis of the sensed information can be performed. Telemetry is further used to communicate information or instructions from external medical devices to the IMD. The IMD includes a telemetry module for performing such telemetry.

Special frequency bands have been allocated for implantable medical devices using RF telemetry such as the MICS (Medical Implantable Communication Service) band ranging from 402-405 MHz and the MEDS (Medical Electronic Data Service) band that extends the range to 401-406 MHz. The limited battery capacity in IMDs presents a challenge in operating a RF transceiver at such frequencies. One manner employed to conserve power in an IMD is to maintain the IMD in an off state and operate in the so-called "sniff" mode. This means that the complete receiver RF portion of the device is turned on for a limited period of time (e.g. 10 milliseconds) during which time the device listens to see if there are any transmitters active in the vicinity wanting to make contact with the IMD. By duty cycling the on (sniff) time heavily with the off time a considerable power saving can be achieved. The signals received during these sniff operations are referred to as wake-up signals that direct the IMD to power on various components to communicate with the external medical device.

SUMMARY

In one or more embodiments, an implantable medical device (IMD) and method are provided in which a telemetry module in the IMD is normally maintained in a low power inactive "sleep" state and powered up to perform sniff operations on communication channels for detecting the presence of wake-up signals. In one or more embodiments, the IMD includes a wake-up signal detector for performing sniff operations in a plurality of different phases that are initiated simultaneously to detect the presence of wake-up signals while differentiating such wake-up signals from noise, interference or other unwanted signals that may be present on the sniffed communication channels. Each one of the phases of sniff operations detects a different signal characteristic.

In one or more embodiments, the plurality of phases of sniff operations includes a first phase for measuring the strength or power of a signal received on a particular channel being sniffed, where it is determined that the received signal is not a wake-up signal if the received signal fails to meet a threshold value comparison and sniff processing is aborted for all phases. The other phases of sniff operations on the particular channel being sniffed are allowed to proceed if the threshold value comparison is met. The plurality of phases of sniff operations includes a second phase for evaluating whether the frequency deviation of the received signal on the channel being scanned is outside of an expected frequency deviation range. If the frequency deviation is outside of the expected range, then it is determined that the received signal is not a wake-up signal and sniff processing is aborted for all phases. If the received signal is within the expected frequency deviation range, then other phases of sniff operations on the particular channel being sniffed are allowed to proceed. The plurality of phases of sniff operations further includes a third phase for demodulating the received signal to detect whether the decoded Manchester-encoded bit stream possesses an acceptable density of Manchester errors, where sniff operations are aborted if the density of Manchester errors exceeds a certain threshold. The duration of the detection procedures of each phase may progressively increase with each successive phase, such that power consumption in the IMD can be conserved by avoiding the need to continue executing the longer detection phases if another detection phase is completed earlier and determines that sniff processing should be aborted due to the detection of an unwanted signal on the communication channel.

In one or more embodiments, a wake-up signal detector for performing sniff operations to detect the presence of a wake-up signal is provided including an integrated frequency deviation (IFD) detector. The IFD detector detects a valid wake-up signal by calculating the integrated frequency deviation of a received signal over a short period and comparing the integrated frequency deviation to corresponding high and low thresholds. Sniff operations are not aborted if the received signal falls between the two thresholds. The integrated frequency deviation calculation is then repeatedly performed in stages with the difference between the high and low thresholds gradually becoming smaller with each subsequent stage. The integrated frequency deviation calculation utilizes an average frequency deviation over the various stages in its calculations to allow the difference between the high and low thresholds to become smaller without the probability of missing a valid wake-up signal. The staged approach of the integrated frequency deviation calculation allows sniff operations to be quickly aborted if it determined in an early stage that a valid wake-up signal is likely not to be present on the channel being sniffed, thereby allowing for a short average decision time while maintaining low probabilities of missing a valid wake-up signal or falsely identifying an unwanted signal as a valid wake-up signal.

In one or more embodiments, a wake-up detector is provided for performing sniff operations to detect the presence of a wake-up signal including a dual frequency modulation (FM) detector configuration to account for frequency deviation in the received signal. The dual FM detector configuration increases the delay in the received signal to correspond to a phase shift of n180°+90° for a given delay (n). The dual FM detector configuration includes a first FM detector that introduces a small delay of 90° into the received signal that is low-pass filtered to provide an estimate of the average center frequency of the received signal, such that the first FM detector serves as a coarse FM detector. The dual FM detector configuration includes a second FM detector with a larger delay (n180°) that is adjusted to account for the average center frequency estimate of the first FM detector, thereby achieving high gain without incurring phase wrapping that is typically associated with such high gain. In one or more embodiments, a look-up table may be utilized by the dual FM detector configuration to determine the appropriate larger delay to be utilized by the second FM detector for the estimated average center frequency of the received signal.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

Since the battery capacity in an IMD is very limited, the power consumed by the components of the IMD can be conserved by keeping the components in a power off or low power "sleep" state when they are not being utilized. The present disclosure describes an implantable medical device (IMD) and a method for operating the same in which a plurality of phases of sniff operations are performed on scanned communication channels to detect the presence of wake-up signals such that power consumption in the IMD can be conserved by allowing sniff operation phases having longer execution times to be aborted when an earlier completed sniff operation phase determines that sniff processing should be aborted due to the detection of an unwanted signal on the communication channel. The present disclosure further describes that one of the sniff operation phases utilizes a phased integrated frequency deviation (IFD) detection procedure that discriminates valid wake-up signals from unwanted signals based upon a staged calculation of the integrated frequency deviation of the received signal that conserves power by providing a short average decision time while maintaining low probabilities of missing a valid wake-up signal or falsely identifying an unwanted signal as a valid wake-up signal. It will be apparent, however, to one skilled in the art, that these and other embodiments may be practiced without these specific details. In some instances, features well-known to those skilled in the art have not been described in detail in order not to obscure the present disclosure.

Figure 1:
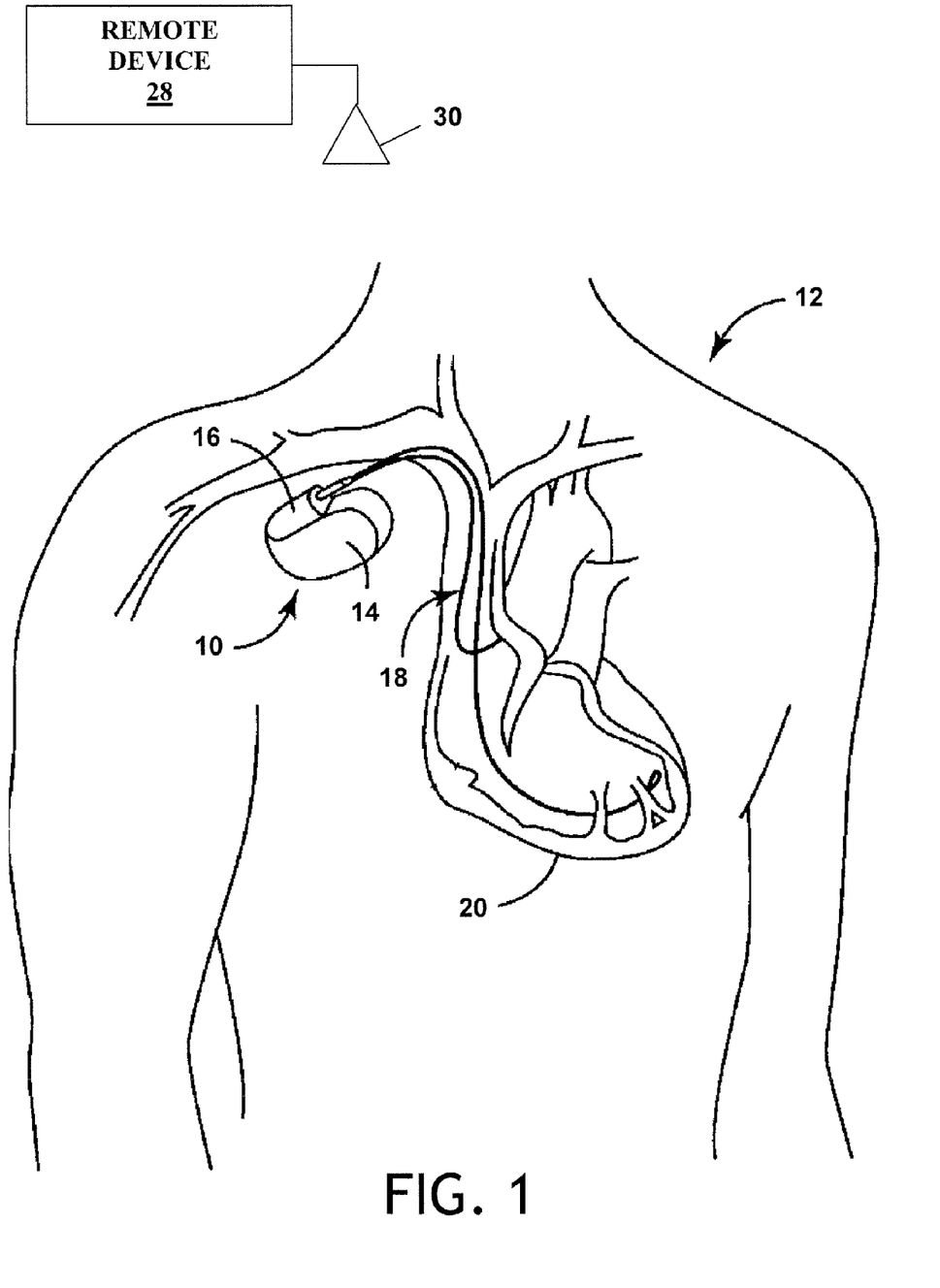
FIG. 1 illustrates an implantable medical device system in accordance with an embodiment of the present disclosure implanted in a human body.

FIG. 1 is a simplified schematic view of one embodiment of implantable medical device ("IMD") 10 of the present disclosure implanted within a human body 12. IMD 10 comprises a hermetically sealed enclosure 14 and connector module 16 for coupling IMD 10 to electrical leads 18 arranged within body 12, such as pacing and sensing leads 18 connected to portions of a heart 20 for delivery of pacing pulses to a patient's heart 20 and sensing of heart 20 conditions. While IMD 10 is depicted in a pacemaker device configuration in FIG. 1, it is understood that IMD 10 may comprise any type of implanted device including, but not limited to implantable cardioverter-defibrillators (ICDs), an implantable combination pacemaker-cardioverter-defibrillator (PCDs), implantable brain stimulators, implantable gastric system stimulators, implantable nerve stimulators or muscle stimulators, implantable lower colon stimulators, implantable drug or beneficial agent dispensers or pumps, implantable cardiac signal loops or other types of recorders or monitors, implantable gene therapy delivery devices, implantable incontinence prevention or monitoring devices, implantable insulin pumps or monitoring devices, and so on.

Figure 2:
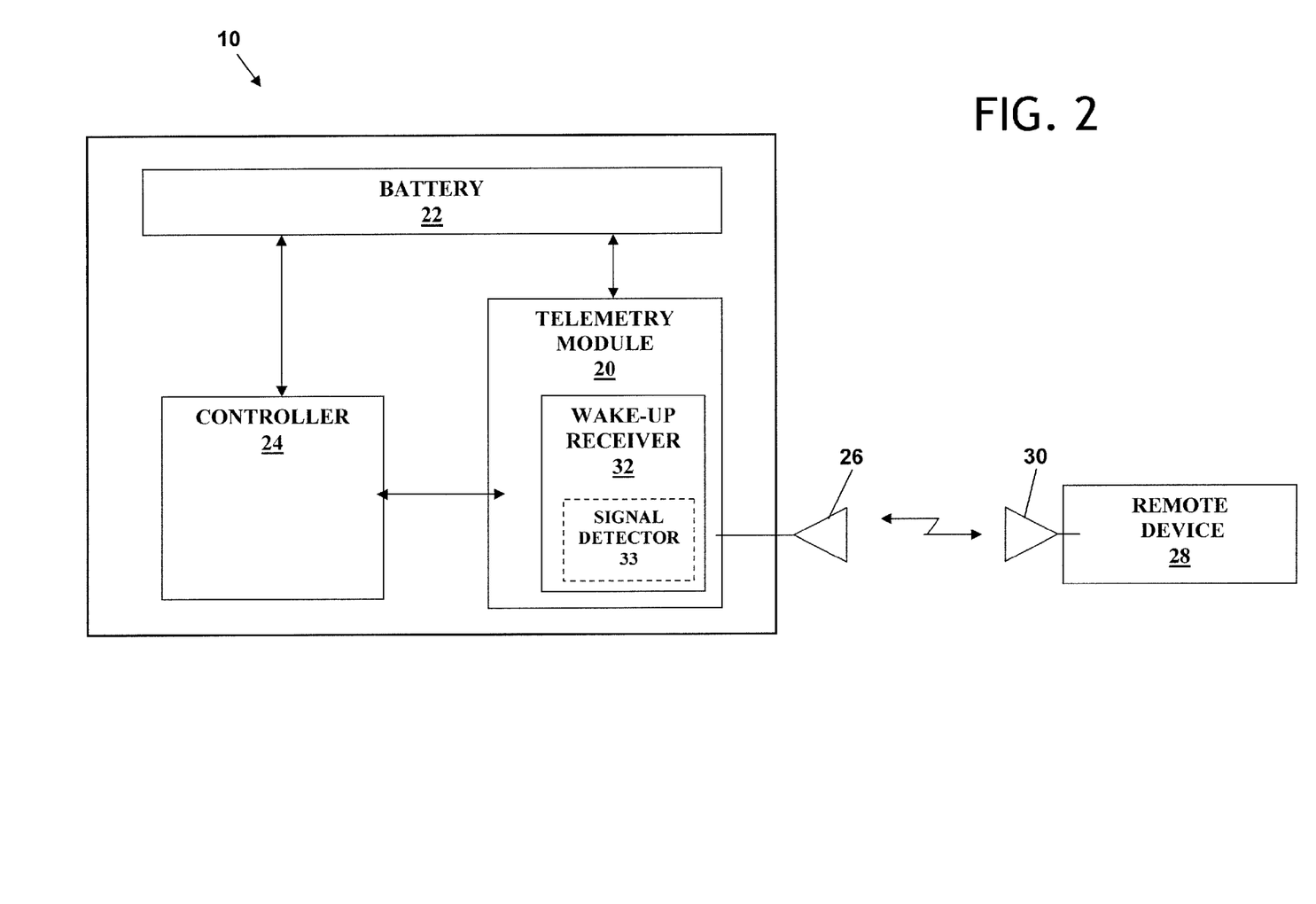
FIG. 2 is a block diagram illustrating the various components of one embodiment of an implantable medical device configured to operate in accordance with the present disclosure.

FIG. 2 is a block diagram illustrating the constituent components of IMD 10 in accordance with one embodiment having a microprocessor-based architecture. IMD 10 is shown as including a telemetry module 20, a battery 22, and a controller 24.

Telemetry module 20 may comprise any unit capable of facilitating wireless data transfer between IMD 10 and an remote device 28, where remote device 28 may comprise an external medical device, a programming device, a remote telemetry station, a base station for IMD 10, a physician-activated device, a patient-activated device, a display device or any other type of device capable of sending and receiving signals to and from IMD 10. Telemetry module 20 and remote device 28 are respectively coupled to antennas 26 and 30 for facilitating the wireless data transfer. Telemetry module 20 may be configured to perform any type of wireless communication. For example, telemetry module 20 may send and receive radio frequency (RF) signals, infrared (IR) frequency signals, or other electromagnetic signals. Any of a variety of modulation techniques may be used to modulate data on a respective electromagnetic carrier wave. Alternatively, telemetry module 20 may use sound waves for communicating data, or may use the patient's tissue as the transmission medium for communicating with a programmer positioned on the patients skin. In any event, telemetry module 20 facilitates wireless data transfer between IMD 10 and remote device 28. Telemetry module 20 includes wake-up receiver 32 for monitoring received communication signals and detecting whether incoming wake-up communication signals are being received from remote device 28. Wake-up receiver 32 may include one or more signal detectors 33 for detecting various signal quantity characteristics in the incoming communication signals.

Controller 24 may comprise any of a wide variety of hardware or software configurations capable of executing algorithms to control telemetry module 20, wake-up receiver 32, and other components. Example hardware implementations of controller 24 include implementations within an application specific integrated circuit (ASIC), a field programmable gate array (FPGA), a programmable logic device, specifically designed hardware components, one or more processors, or any combination thereof. If implemented in software, a computer readable medium, such as a memory in the IMD 10, may store computer readable instructions, e.g., program code, that can be executed by controller 24 to carry out one or more of the techniques described herein. For example, the memory may comprise random access memory (RAM), read-only memory (ROM), non-volatile random access memory (NVRAM), electrically erasable programmable read-only memory (EEPROM), flash memory, or the like. Telemetry module 20 may likewise comprise any of a wide variety of the above-listed hardware or software configurations capable of executing algorithms for facilitating wireless telemetry.

IMDs typically must rely entirely on an implanted power source, e.g., battery 22. It is desirous to keep the physical size of IMD 10 to a minimum, which further places limitations on the size of the implanted battery 22. The various components of IMD 10 (i.e., telemetry module 20, controller 24, wake-up receiver 32) rely on battery 22 for power. For embodiments of IMD 10 that have nonrechargeable batteries 22, IMD 10 typically must be surgically replaced when battery 22 is fully depleted. For embodiments of IMD 10 having rechargeable batteries 22, a surgical procedure is not required when battery 22 is depleted, however, battery 22 must be recharged more frequently since it cannot store as much energy. Thus, power conservation is particularly important in IMD 10. Further, consistently powering up wake-up receiver 32 of telemetry module 20 to perform sniff operations requires electrical power which can drain battery 22 of IMD 10 at an unacceptable rate.

In one or more embodiments, IMD 10 and a method for operating the same is provided in which telemetry module 20 is normally maintained in a power off or low power inactive "sleep" state in order to conserve power. Wake-up receiver 32 is then periodically powered up to perform sniff operations in which wake-up receiver 32 monitors communication channels in the desired communication frequencies (e.g., MICS band, MEDS band or any other frequency bands) to detect wake-up communication signals or other types of communication signals being received from remote device 28. If a communication signal from remote device 28 is detected during these sniff operations, it is determined that remote device 28 is either attempting to communicate with IMD 10 or remote device 28 is within telemetry range capable of communicating with IMD 10 (e.g., remote device 28 is transmitting beacon signals that are being received by IMD 10). IMD 10 can then power up ("wake-up") the necessary components required to transmit or receive data from remote device 28.

For typical RF communications, given the plethora of noise, interference sources, and other extraneous signals that exist (collectively referred to hereafter as "unwanted signals"), wake-up receiver 32 could unnecessarily consume current and thus waste the limited power resources of battery 22 if it were to implement detection procedures to discover whether these unwanted signals are actually wake-up signals. Thus, in accordance with one or more embodiments, a plurality of detection phases are employed by the components of wake-up receiver 32, such as in signal detector 33, that reduce power consumption in IMD 10 during sniff operations by immediately aborting sniff operations as early in the sniff operations as it is determined that the received communication signal is an unwanted signal.

In one or more embodiments, a sniff on a communication channel is processed in a plurality of detection phases in which each detection phase measures a different characteristic of a received signal to detect whether the received communication signal is a wake-up communication signal. When measuring a quantity of a signal, such as its RF power or the frequency deviation of the signal, the standard deviation of the measurement is reduced as the measuring time or number of measurements are increased. However, measuring signal quantities for longer periods of time or performing longer, more complex analyses also requires greater current consumption by the signal detector 33. Thus, in one or more embodiments, wake-up receiver 32 employs a phased detection process in which the average sniff time is reduced by avoiding having to complete the execution of longer detection phases if another detection phase is completed earlier and determines that sniff processing should be aborted due to the detection of an unwanted signal on the communication channel.

Figure 3:
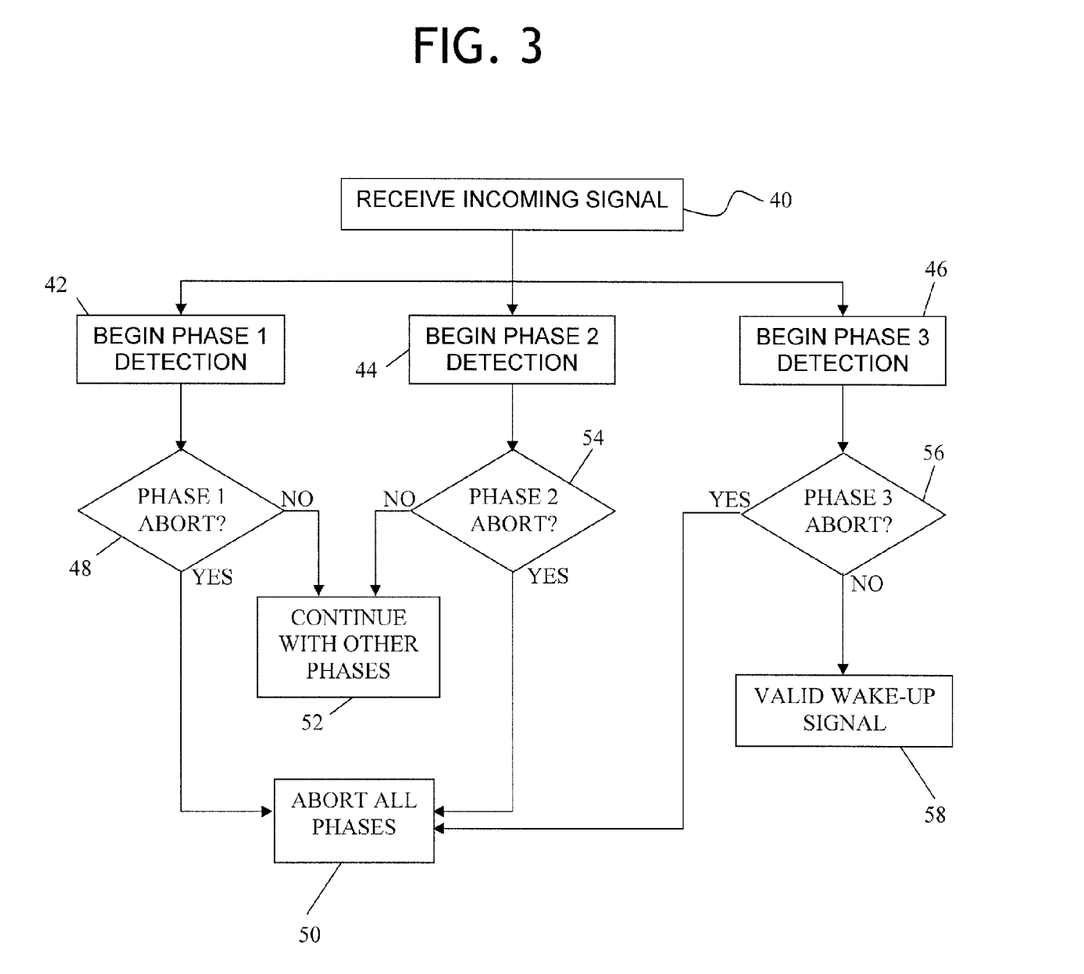
FIG. 3 is an operational flow diagram illustrating a process for operating the wake-up receiver in accordance with one embodiment of the present disclosure.

In one or more embodiments, wake-up receiver 32 employs a plurality of phases of sniff operations that are initiated simultaneously, as illustrated in the operational flow diagram of FIG. 3. For an incoming signal that is received (40) on a channel being sniffed, the plurality of phases of sniff operations includes a first phase (Phase 1) that is initiated (42) to measure the strength or power of the received signal to determine whether it meets a certain threshold values required for valid wake-up signals. If it is determined (48) that the received signal is not a wake-up signal because the received signal fails to satisfy the threshold comparison requirements, sniff processing is aborted (50) for all the phases of sniff operations on that channel. If the threshold comparison is satisfied (48), then the other phases of sniff operations on the particular channel being sniffed are allowed to continue to proceed (52). In one or more embodiments, the plurality of phases of sniff operations includes a second phase (Phase 2) that is initiated (44) simultaneously with Phase 1 for evaluating whether the frequency deviation of the received signal on the channel being scanned is outside of a certain frequency deviation range. If it is determined (54) that the frequency deviation is outside of the certain frequency deviation range, then it is determined that the received signal is not a wake-up signal and sniff processing is aborted (50) for all phases. If it is determined (54) that the received signal is within the expected frequency deviation range, then other phases of sniff operations on the particular channel being sniffed are allowed to proceed (52). The plurality of phases of sniff operations further includes a third phase (Phase 3) that is initiated (46) simultaneously with the other phases for demodulating the received signal to ensure that the decoded Manchester encoded bit stream possesses an acceptable density of Manchester errors (e.g., number of errors over a given number of bits). If it is determined (56) that the Manchester decoded received signal possesses a density of Manchester decoding errors exceeding a certain threshold, then Phase 3 is aborted (50). If any of the other phases are still performing their determinations when Phase 3 is aborted, all of the other phases of sniff operations on that particular channel are also aborted at that time. If an acceptable density of Manchester decoding errors is present, then all 3 phases have passed and it is determined that the received signal is a valid wake-up signal (58).

In one or more embodiments, the duration of the detection procedures of each phase may be different than the other phases, such that some phases of sniff operations may still be in progress when one of the other phases reaches an abort decision. The other phases still in progress can thus abort their detection procedure prior to their completion, thereby conserving power in IMD 10. Power consumption in IMD 10 is conserved by avoiding the need to continue executing longer detection phases as soon as another detection phase is completed earlier and determines that sniff processing should be aborted due to the detection of an unwanted signal on the communication channel. In one or more embodiments, the duration of the detection procedures of each phase may be increase with each successive phase such that the accuracy of the determination that the received signal is a valid wake-up signal also increases with each successive phase.

Figure 4:
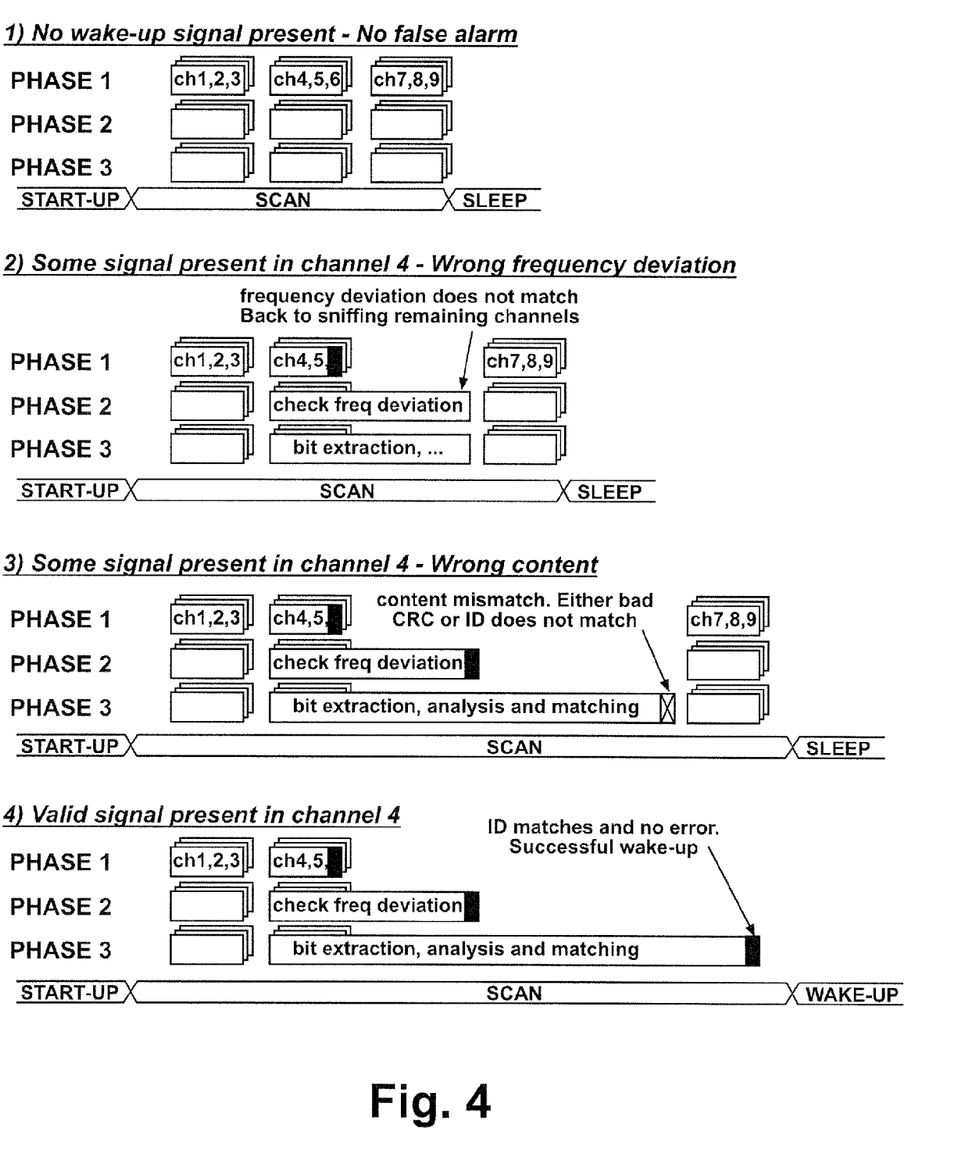
FIG. 4 is a schematic illustration of the durations of various phases of sniff operations in accordance with one embodiment of the present disclosure.

Referring now to FIG. 4, a schematic illustration is provided illustrating various representative examples of the durations of the various phases of sniff operations when encountering different received signals on the channel being sniffed. In example situation 1) of FIG. 4, no signal is present on the sniffed channel so the received signal strength threshold of Phase 1 is not satisfied, thereby causing Phases 2 and 3 to abort their detection procedures at the same time as Phase 1 is complete. In example situation 2), there is some signal present on the channel being sniffed but it possesses the wrong frequency deviation. Thus, the signal strength of the received signal passes the Phase 1 determination in this case and continues with Phases 2 and 3. However, Phase 2 aborts its sniff operations procedure as soon as it determines that the frequency deviation is outside of the expected frequency deviation range, which also results in Phase 3 aborting its sniff operations at the same time for that channel. In example situation 3), the received signal possesses the desired signal strength and frequency deviation but it does not possess the proper Manchester-encoded content. Thus, Phases 1 and 2 allow Phase 3 to continue with its detection procedure, but Phase 3 eventually aborts its sniff operations on this channel when its detection procedures are not satisfied. In example situation 4), the received signal is a valid wake-up signal and it can be seen that all 3 Phases are performed until complete, at which point the wake-up signal is detected and wake-up procedures are initiated. From these examples, it can be seen that sniff operations on the channel being scanned can be aborted early if one of the earlier-completed phases makes a determination that a wake-up signal is not present, such that over time the average scan time of the sniff operations can be reduced which, in turn, also reduces power consumption in IMD 10.

Figure 5A:
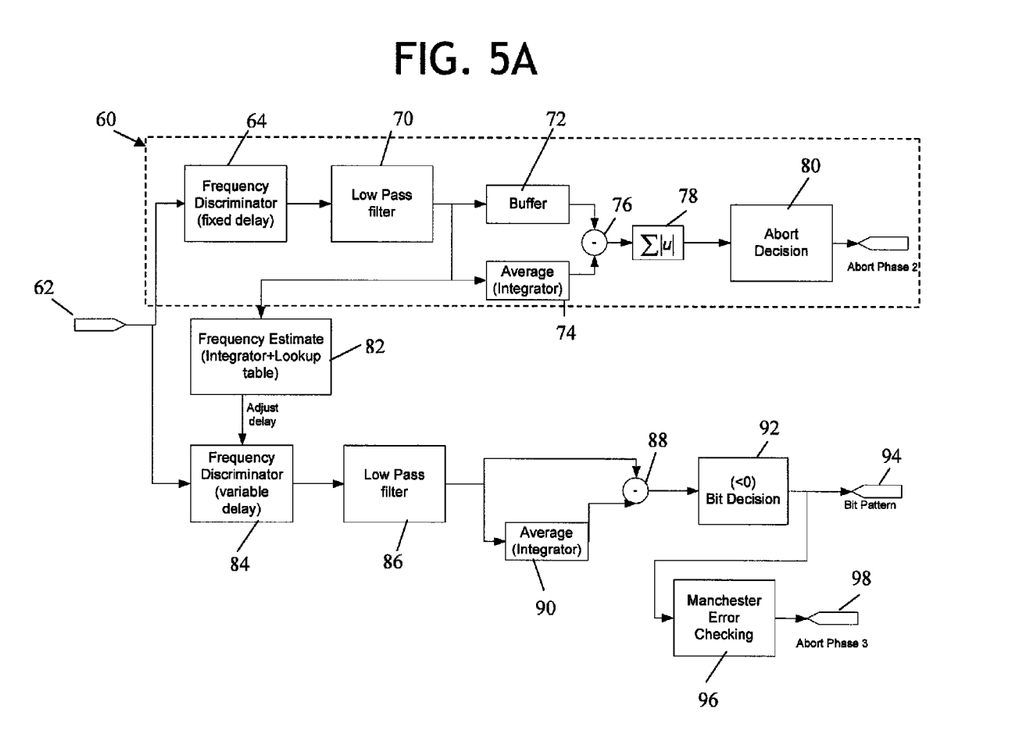
FIG. 5A is a block schematic circuit diagram illustrating the various components of one embodiment of the integrated frequency deviation detector and dual FM detector of the wake-up receiver of the implantable medical device configured to operate in accordance with the present disclosure.

In one or more embodiments, signal detector 33 in wake-up receiver 32 may include an integrated frequency deviation (IFD) detector 60 for evaluating the frequency deviation of the received signal during a phase of sniff operations (e.g., Phase 2) to detect the presence of a wake-up signal. FIG. 5A illustrates a block schematic circuit illustration of an IFC detector 60. IFD detector 60 detects a valid wake-up signal by calculating the integrated frequency deviation of a received signal over a short period and comparing the integrated frequency deviation to corresponding high and low threshold values. Sniff operations are not aborted if the frequency deviation of the received signal is determined to fall between the two thresholds. In one or more embodiments, the integrated frequency deviation calculation is then repeatedly performed in stages with the difference between the high and low thresholds gradually becoming smaller with each subsequent stage and the distributions becoming tighter. The integrated frequency deviation calculation utilizes an average frequency deviation over the various stages in its calculations to allow the difference between the high and low thresholds to become smaller whilst maintaining a low probability of missing a valid wakeup signal. The staged approach of the integrated frequency deviation calculation allows sniff operations to be quickly aborted if it determined at an early stage that a valid wake-up signal is likely not to be present on the channel being sniffed, thereby allowing for a short average decision time while maintaining low probabilities of missing a valid wake-up signal or falsely identifying an unwanted signal as a valid wake-up signal.

Figure 5B:
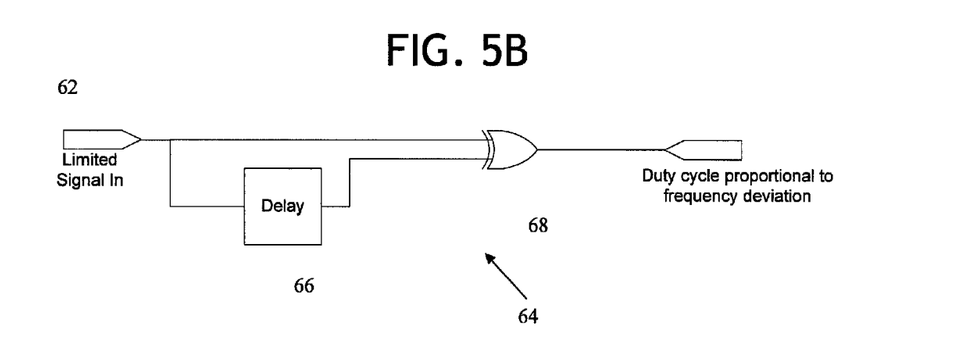
FIG. 5B is a block schematic circuit diagram illustrating the frequency discriminator of FIG. 5A in accordance with one embodiment of the present disclosure.

With specific reference to the components of FIG. 5A, a received signal on the channel being sniffed is received at input 62 of IFD detector 60 and fed into a frequency discriminator 64 having a fixed delay. As more specifically illustrated in the block schematic illustration of FIG. 5B, the frequency discriminator 64 includes a delay component 66 and an XOR component 68 that converts the frequency variation in the received signal into a duty cycle that is proportional to the frequency variation. A low pass filter 70 then attenuates the 2IF information from the signal while keeping the frequency modulation information. In one or more embodiments, the low-pass filter may comprise a $5^{th}$ order Slink filter. In one or more embodiments, a plurality of successive output values from the low-pass filter 70 (e.g., 16 successive output values over 3.2 bit periods) of the received signal are stored in buffer 72 while the average over the same plurality of successive samples is calculated by an Integrator 74 or other similar components for computing an average value. The difference between the buffered output values and the average value is computed at 76, and the total distance between the average and actual frequency deviation is then calculated by the components in block 78. This total distance (called 'Sum') is the figure of merit used for the Phase 2 frequency deviation decision making. For 16 successive output values, the Sum is represented by the following equation:

$$\text{Sum} = \sum_{i=1}^{16} |\Delta f_1 - \overline{\Delta f}| = \sum_{i=1}^{16} \left| \Delta f_1 - \frac{1}{16} \cdot \sum_{i=1}^{16} \Delta f_i \right|$$

The Sum is then compared against corresponding high and low thresholds by the components in the Abort Decision block 80. Sniff operations are not aborted if the frequency deviation of the received signal is determined to fall between the two thresholds. In one or more embodiments, the duration of the algorithm employed by IFD detector 60 may include an initialization period of 5 samples for the low pass filter 70 and between 1 to 3 sets of 16 samples are used to calculate the Sum value from the equation above. Each of these calculations will take slightly longer than the 16 samples as time is needed to process the Sum equation, and the total duration of extra processing is approximately 1 sample. This extends the total duration of each stage of the IFD algorithm of Phase 2 to be approximately 17 samples (or 3.4 bits) in the situation where 16 successive output values are selected. However, it is understood that any number of successive output values from the low-pass filter 70 can be selected and that the Sum calculation can be made using other numbers of successive output values other than 16.

In one or more embodiments, the integrated frequency deviation determination performed by IFD 60 can be performed as a staged decision by repeatedly performing the integrated frequency deviation determination in stages with the difference between the high and low thresholds gradually becoming smaller or tighter with each subsequent stage. The integrated frequency deviation determination would utilize an average frequency deviation over the various stages in its calculations to allow the difference between the high and low thresholds to become smaller whilst maintaining a low probability of missing a valid wakeup signal. The staged approach of the integrated frequency deviation calculation allows sniff operations to be quickly aborted if it determined at an early stage that a valid wake-up signal is likely not to be present on the channel being sniffed, thereby allowing for a short average decision time while maintaining low probabilities of missing a valid wake-up signal or falsely identifying an unwanted signal as a valid wake-up signal.

Figure 6A:
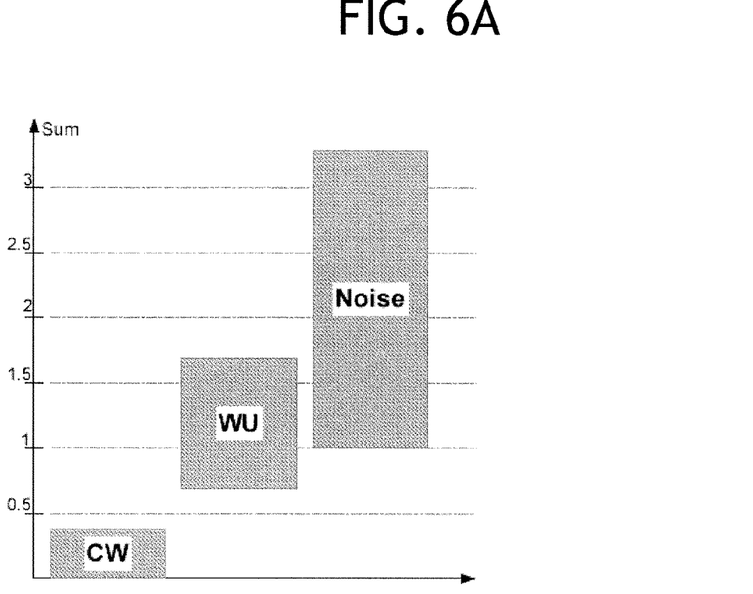
FIGS. 6A and 6B are graphical illustrations of Sum values for different signals for stages of sniff operations in accordance with one embodiment of the wake-up receiver of the implantable medical device of the present disclosure.
Figure 6B:
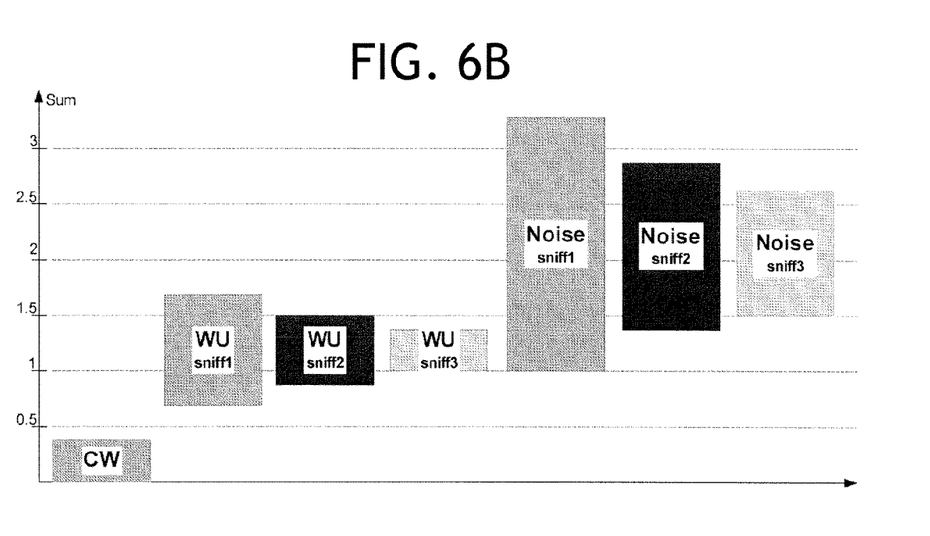

Referring now to the graphical illustrations of FIGS. 6A and 6B, the responses of the Phase 2 IFD detector 60 for 1 sniff stage (FIG. 6A) and for 3 sniff stages (FIG. 6B) are shown to illustrate the tightening of the high and low thresholds with an increased number of stages. In FIG. 6A, the Sum calculation for one sniff of an unmodulated continuous-wave (CW) signal, a valid wake-up (WU) signal and an unwanted noise signal are illustrated. It can be seen that it is easy to distinguish a CW signal from a valid wake-up (WU) signal. However, a valid wake-up (WU) signal and a noise signal can return a value falling in overlapping Sum ranges of FIG. 6A. If the high and low thresholds for one sniff are set to Sum values of 0.5 and 1.7, the probability of receiving a false alarm ($P_{FA}$) by detecting a CW signal as a wake-up signal is $P_{FA}$ (CW)=0 while the probability of receiving a false alarm by detecting noise as a wake-up signal is relatively large.

Referring now to FIG. 6B, the Sum calculation for three stages of sniffs of an unmodulated continuous-wave (CW) signal, a valid wake-up (WU) signal and an unwanted noise signal are illustrated. The principle of the algorithm employed by IFD detector 60 is to release the decision (e.g., abort the sniff operation or allow the Phase 2 determination to pass) as soon as it can be made with a high confidence level. In this representative example, the high and low thresholds are set as Sum<0.5 (CW) or Sum>1.65 (Noise). If the Sum value is in between these two threshold limits, a second sniff is performed and the difference between the thresholds is tightened, which eliminates some of the noise cases for $P_{FA}$ (noise). Finally, a third sniff is performed for the remaining cases with yet a further tightened difference between the thresholds. It can be seen that averaging the Sum calculations over multiple stages makes the Sum distributions tighter. The effects of the staged decision performed for the integrated frequency deviation determination performed by IFD 60 are much lower probabilities of false alarms of valid wake-up signals at the cost of slightly longer sniff times. For example, in the representative examples illustrated in FIGS. 6A and 6B, the probability of receiving a false alarm by detecting noise as a wake-up signal is significantly reduced (e.g., from 50% to less than 10%) by performing 3 sniffs as compared to 1 sniff.

In one or more embodiments, signal detector 33 in wake-up receiver 32 may include a dual frequency modulation (FM) detector configuration to account for frequency deviation in the received signal, as further illustrated the block schematic illustration of FIG. 5A. The dual FM detector configuration includes a first FM detector having a small delay that can accommodate a large frequency variation in the received signal, where the first FM detector serves as a coarse FM detector that provides an estimate of the average frequency of the received signal. The dual FM detector configuration also includes a second FM detector having a larger delay that provides extra gain to greatly improve and lower the bit error rate, where the delay of the second FM detector is adjusted by the average frequency estimate of the first FM detector 82.

In one or more embodiments, the first FM detector (e.g., frequency discriminator 64 of FIG. 5A) introduces a small delay of 90° into the received signal, which is then passed through a low-pass filter 70 to remove the 2IF component of the signal. The output of the low-pass filter 70 provides an estimate of the average center frequency of the received signal to block 82. The estimated average center frequency is then input into the second FM detector (e.g., frequency discriminator 84 having a variable delay). The second FM detector 84 then introduces a larger delay of n180° into the received signal for a selected delay (n), where the optimal value of (n) is selected from a look-up table in block 82 based on the estimated average center frequency. Thus, the output of the second FM detector 84 increases the delay in the received signal to correspond to a phase shift of n180°+90° for a given delay (n). This dual FM detector configuration is able to achieve high gain with an improved bit error rate without incurring phase wrapping typically associated with such a large phase shift.

The output signal can then be further processed to detect whether the decoded Manchester-encoded bit stream possesses an acceptable density of Manchester errors indicating the detection of a valid wake-up signal (i.e., the Phase 3 determination described above). In one or more embodiments, this further signal processing may include filtering the output signal with low pass filter 86. A difference 88 between the filtered signal and an integrated average value of the received signal computed at block 90 is performed, where the frequency deviation is used in the bit decision block 92 to identify the bit pattern 94. Manchester error checking is performed on the decoded bit stream by the components of block 96 to determine whether the bit stream possesses an acceptable density of Manchester errors indicating the detection of a valid wake-up signal or whether Phase 3 should be aborted 98.

While the system and method have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A method comprising:
   operating a device capable of receiving wireless communication signals; and
   monitoring a selected communication channel with an integrated frequency deviation signal detector to detect whether a wireless communication signal being received over the selected communication channel is a desired communication signal;
   wherein the integrated frequency deviation signal detector monitors the selected communication channel by:
      calculating the integrated frequency deviation of a received signal;
      comparing the integrated frequency deviation against corresponding high and low threshold values; and
      determining that the received signal is not a desired communication signal if the integrated frequency deviation fails to fall between the corresponding high and low threshold values;

wherein the device is an implantable medical device, the method further comprising:

performing a plurality of different phases of sniff operations in an implantable medical device for detecting whether a wake-up communication signal is being received by the implantable medical device over a selected communication channel, wherein one of the phases of sniff operations comprises the monitoring the selected communication channel performed by the integrated frequency deviation signal detector, the method further aborting all of the different phases of sniff operations on the selected communication channel if the integrated frequency deviation fails to fall between the corresponding high and low threshold values.

2. The method of claim 1, wherein integrated frequency deviation signal detector monitors the selected communication channel by repeatedly performing the integrated frequency deviation calculation and threshold comparison steps in a plurality of stages with the difference between the corresponding high and low threshold values becoming smaller with each subsequent stage.

3. The method of claim 2, wherein the integrated frequency deviation calculation calculates an average frequency deviation from all completed stages.

4. The method of claim 1, wherein the device is an implantable medical device, the method further comprising determining whether the received signal is a wake-up signal for the implantable medical device.

5. The method of claim 1, wherein one of the phases of sniff operations comprises a Manchester decoding phase that uses a dual frequency modulation (FM) detector configuration to detect whether a decoded Manchester encoded bit stream possesses a density of Manchester errors below a certain threshold indicating the detection of a wake-up communication signal.

6. The method of claim 5, wherein the Manchester decoding phase further comprises:

introducing a delay into the received signal using a first FM detector;

low pass filtering the output of the first FM detector to provide an estimate of the average center frequency of the received signal;

introducing a second delay into the received signal using a second FM detector, wherein the second delay introduced by the second FM detector is larger than the delay introduced by the first FM detector and wherein the second delay is dependent upon the estimated average center frequency.

7. The method of claim 6, wherein a total delay introduced into the received signal is equal to a phase shift of n180°+90°, wherein the first FM detector introduces a delay of 90° and the second FM detector introduces a delay of n180° for a selected delay (n) that is selected based upon the estimated average center frequency.

8. A frequency discriminator for discriminating a desired signal from unwanted signals on a communication channel, comprising:

an integrated frequency deviation signal detector for monitoring a selected communication channel to detect whether a signal being received over the selected communication channel is a desired signal, wherein the integrated frequency deviation signal detector is configured to:

calculate the integrated frequency deviation of a received signal;

compare the integrated frequency deviation against corresponding high and low threshold values; and determine that the received signal is not a desired signal if the integrated frequency deviation fails to fall between the corresponding high and low threshold values;

wherein the frequency discriminator is contained within a wake-up receiver of an implantable medical device, the wake-up receiver including a plurality of signal detectors configured to perform a plurality of different phases of sniff operations in the implantable medical device for detecting whether a wake-up communication signal is being received by the implantable medical device over a selected communication channel, wherein one of the phases of sniff operations is performed by the integrated frequency deviation signal detector that is further configured to abort all of the different phases of sniff operations on the selected communication channel if the integrated frequency deviation fails to fall between the corresponding high and low threshold values.

9. The frequency discriminator of claim 8, wherein the integrated frequency deviation signal detector is further configured to repeatedly perform the integrated frequency deviation calculation and threshold comparison steps in a plurality of stages with the difference between the corresponding high and low threshold values becoming smaller with each subsequent stage.

10. The frequency discriminator of claim 9, wherein the integrated frequency deviation signal detector is further configured to calculate the integrated frequency deviation calculation using an average frequency deviation from all completed stages.

11. The frequency discriminator of claim 8, wherein the frequency discriminator is contained within an implantable medical device and wherein the frequency discriminator determines whether the received signal is a wake-up signal for the implantable medical device.

12. The frequency discriminator of claim 8, wherein the wake-up receiver includes a dual frequency modulation (FM) detector configuration configured to perform one of the phases of sniff operations comprising a Manchester decoding phase that detects whether a decoded Manchester encoded bit stream possesses a density of Manchester errors below a certain threshold indicating the detection of a wake-up communication signal.

13. The frequency discriminator of claim 12, wherein the dual frequency modulation (FM) detector configuration comprises:

a first FM detector configured to introduce a delay into the received signal;

a low pass filter connected to the output of the first FM detector to provide an estimate of the average center frequency of the received signal;

a second FM detector configured to introduce a second delay into the received signal, wherein the second delay introduced by the second FM detector is larger than the delay introduced by the first FM detector and wherein the second delay is dependent upon the estimated average center frequency.

14. The frequency discriminator of claim 13, wherein the dual frequency modulation (FM) detector configuration introduces a total delay into the received signal equal to a phase shift of n180°+90°, wherein the first FM detector introduces a delay of 90° and the second FM detector introduces a delay of n180° for a certain delay (n) that is selected based upon the estimated average center frequency.

15. The frequency discriminator of claim 12, wherein the wake-up receiver includes a signal strength detector configured to perform a signal strength detecting phase during one of the phases of sniff operations,
wherein the signal strength detector is further configured to abort all of the different phases of sniff operations on the selected communication channel if a measured signal strength in the signal strength detecting phase fails to meet a threshold value determination.

* * * * *